United States Patent [19]
Chen

[11] Patent Number: 6,080,197
[45] Date of Patent: Jun. 27, 2000

[54] SHOCK ABSORBING DEVICE FOR AN ARTIFICIAL LEG

[75] Inventor: Sen-Jung Chen, Taipei, Taiwan

[73] Assignee: Teh Lin Prosthetic & Orthopaedic Inc., Taipei, Taiwan

[21] Appl. No.: 09/134,509

[22] Filed: Aug. 13, 1998

[51] Int. Cl.[7] ............................ A61F 2/64; A61F 2/66; F16F 5/00; F16M 1/00
[52] U.S. Cl. ........................... 623/27; 623/47; 623/52; 267/118; 267/140.5
[58] Field of Search ..................... 623/47, 52, 27, 623/36, 35, 49, 50; 138/26; 49/9; 188/268; 267/140.5, 195, 2, 190, 34, 226

[56] References Cited

U.S. PATENT DOCUMENTS

| | | | |
|---|---|---|---|
| 3,885,776 | 5/1975 | Blatt | 267/34 |
| 4,318,535 | 3/1982 | Imai | 267/8 R |
| 4,370,761 | 2/1983 | Serri | 3/26 |
| 4,446,580 | 5/1984 | Furuya et al. | 623/27 |
| 5,405,411 | 4/1995 | McCoy | 623/49 |
| 5,458,656 | 10/1995 | Phillips | 623/27 |
| 5,702,488 | 12/1997 | Wood et al. | 623/27 |
| 5,888,239 | 3/1999 | Wellershaus et al. | 623/55 |
| 5,961,556 | 10/1999 | Thorn | 623/27 |
| 5,984,972 | 11/1999 | Huston et al. | 623/35 |

*Primary Examiner*—Mickey Yu
*Assistant Examiner*—Alvin Stewart
*Attorney, Agent, or Firm*—Christie, Parker & Hale, LLP

[57] ABSTRACT

A shock absorbing device for use with an artificial leg has a coupling member that includes a mounting plate and a tubular portion. The tubular portion has an upper end surface and is formed with a radial inward first restricting portion distal to the upper end surface. A sleeve member has a lower sleeve portion mounted telescopically on the tubular portion, and an upper sleeve portion formed with a radial inward second restricting portion that is disposed above the upper end surface of the tubular portion of the coupling member. A damping member extends into the coupling member and the sleeve member between the first and second restricting portions. A cushioning unit is provided for cushioning axial and radial forces exerted on the coupling member and the sleeve member, and for defining an upper limit of the relative axial movement between the coupling member and the sleeve member.

7 Claims, 6 Drawing Sheets

SHOCK ABSORBING DEVICE FOR AN ARTIFICIAL LEG

BACKGROUND OF THE INVENTION

1. Field of the Invention

The invention relates to a shock absorbing device, more particularly to a device for absorbing and dissipating both shock and shear forces acting on an artificial leg.

2. Description of the Related Art

Conventionally, an artificial limb is fitted to the stump of an amputee through a socket or other connecting means. The constituting parts of an artificial limb depend on the condition of the stump. For example, in case a lower limb is amputated from the hip area or from above the knee, the connecting means for the stump, such as a socket, is coupled with a prosthesis consisting of a thigh member, a knee member, a shin member, an ankle member and a foot member. Since the thigh and shin members are normally made into a rigid structure, the movement of an artificial leg can only be achieved by pivoting motion of the knee and ankle members. Moreover, only back and forth movement is permitted in the articulation of the knee and ankle members due to limitations imposed by the operating and spatial arrangement of the associated elements. That is to say, axial motion is not allowed in the artificial leg. Because of this restriction, excess terminal impact acting on the foot member cannot be absorbed or dissipated and will be transferred completely to the stump, thereby resulting in discomfort and pain to the amputee.

SUMMARY OF THE INVENTION

Therefore, the main object of the present invention is to provide a device for absorbing shock that acts on an artificial lower limb.

Accordingly, the shock absorbing device of this invention is adapted for use with an artificial leg, and comprises a coupling member, a sleeve member, a damping member and a cushioning unit. The coupling member includes a horizontal mounting plate and a tubular portion that extends vertically from the mounting plate. The tubular portion has an upper end surface and is formed with a radial inward first restricting portion distal to the upper end surface. The sleeve member has a lower sleeve portion mounted telescopically on the tubular portion, and an upper sleeve portion formed with a radial inward second restricting portion that is disposed above the upper end surface of the tubular portion of the coupling member. The damping member extends into the coupling member and the sleeve member, and has a lower end that abuts against the first restricting portion and an upper end that abuts against the second restricting portion. The damping member is capable of damping axial forces exerted on the coupling member and the sleeve member. The cushioning unit is provided on the coupling member and the sleeve member for cushioning axial and radial forces exerted on the coupling member and the sleeve member, and for limiting relative axial movement between the coupling member and the sleeve member.

Preferably, the cushioning unit includes a cushioning block that projects outwardly from the lower sleeve portion, and an upright retaining member mounted on the mounting plate adjacent to the tubular portion. The retaining member confines a vertical slide channel that opens toward the tubular portion and that receives the cushioning block slidably therein. The slide channel is formed with an upper limiting surface to limit upward vertical sliding movement of the cushioning block relative to the retaining member. The upper limiting surface cooperates with the mounting plate to limit the relative axial movement between the coupling member and the sleeve member.

Through the use of a device according to the foregoing, shock that acts on an artificial limb can be absorbed and dissipated first by the damping member and subsequently by the cushioning block.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
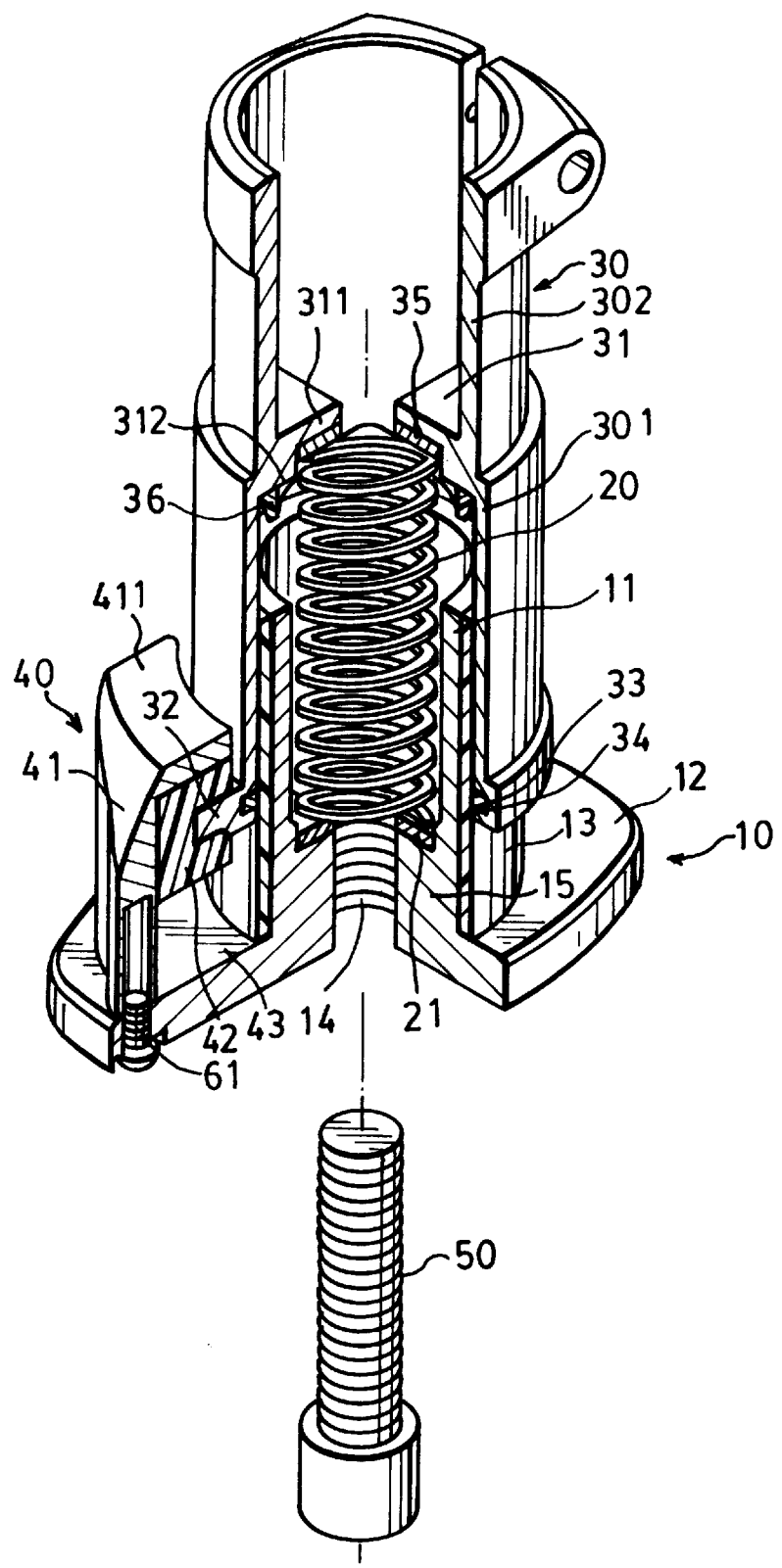
FIG. 1 is a partly sectional, perspective view illustrating a first preferred embodiment of the shock absorbing device according to the present invention.
Figure 2:
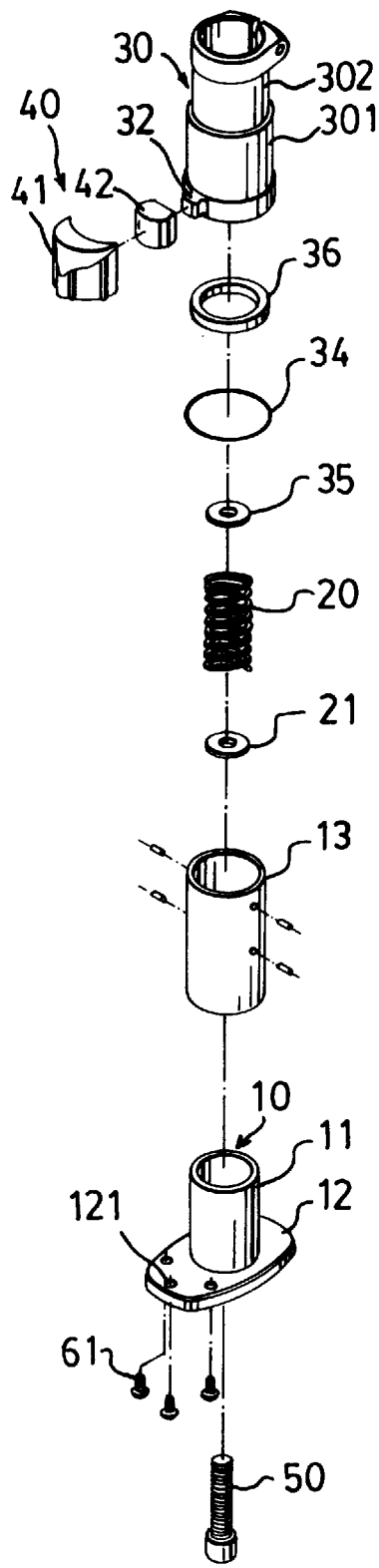
FIG. 2 is an exploded view of the first preferred embodiment of the shock absorbing device according to the present invention.

Referring to FIGS. 1 and 2, the first preferred embodiment of a shock absorbing device according to the present invention is shown to comprise a coupling member 10, a sleeve member 30, a damping member 20 and a cushioning unit 40.

The coupling member 10 includes a horizontal mounting plate 12 and a tubular portion 11 that extends vertically from the mounting plate 12. The tubular portion 11 is formed with a radial inward first restricting portion 15 distal to an upper end surface thereof.

The sleeve member 30 has an upper sleeve portion 302, and a lower sleeve portion 301 mounted telescopically on the tubular portion 11. The upper sleeve portion 302 is formed with a radial inward second restricting portion 31 that is disposed above the upper end surface of the tubular portion 11 of the coupling member 10. The lower sleeve portion 301 is formed with a radial outward flange 32, the purpose of which will be described hereinafter.

A lubricating bushing 13, such as one made from Teflon, is disposed around the tubular portion 11 and inside the lower sleeve portion 301. In addition, a resilient ring 34 is mounted in an annular groove 33 formed in the inner wall surface of the lower sleeve portion 301 and is in contact with the lubricating bushing 13.

Figure 5:
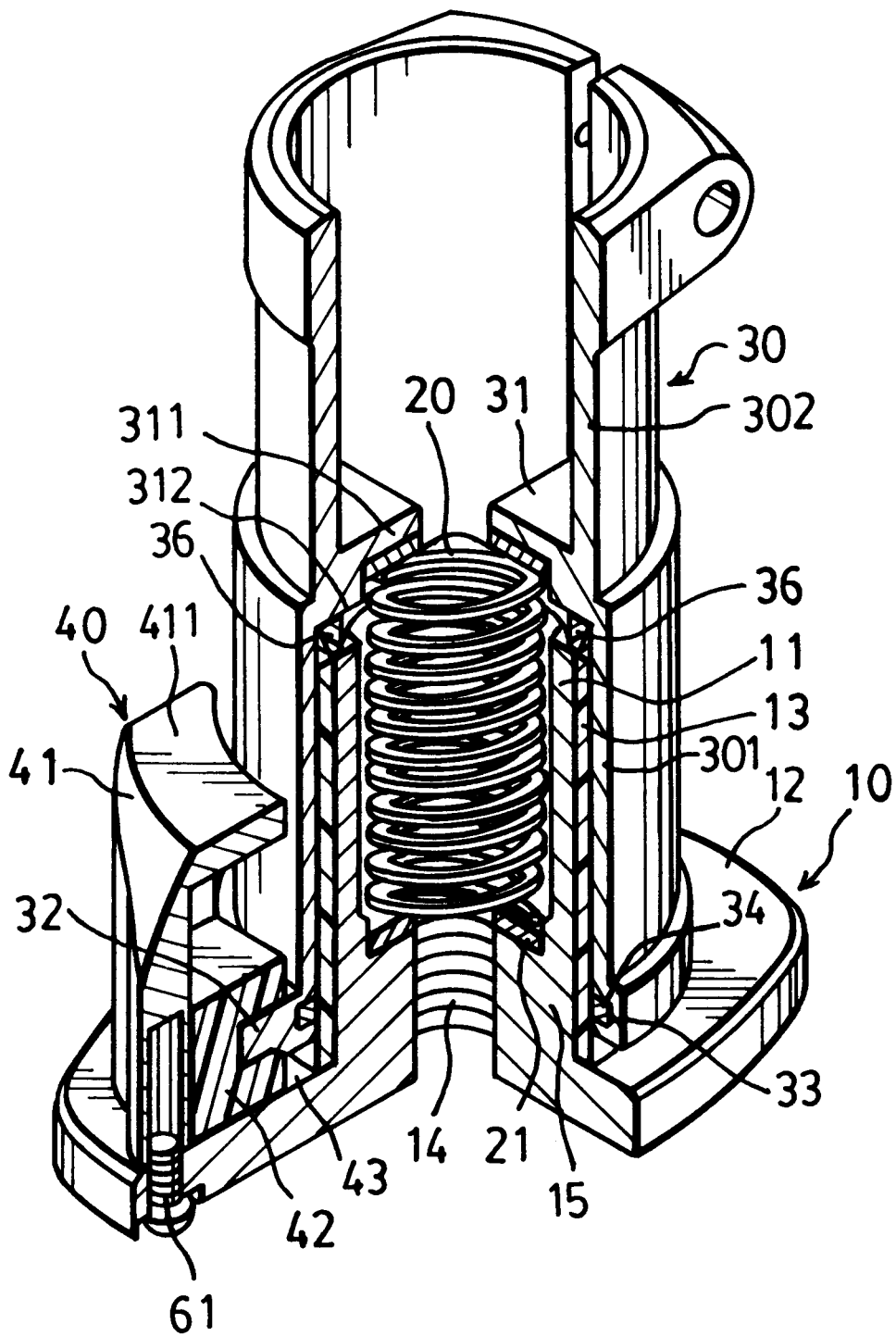
FIG. 5 is a partly sectional, perspective view of the first preferred embodiment, wherein the sleeve member slides to a lower limit with respect to the coupling member.

The damping member 20 in this embodiment is a coiled compression spring that is extended into the coupling member 10 and the sleeve member 30. The damping member 20 has a lower end that abuts against the first restricting portion 15, and an upper end that abuts against the second restricting portion 31. The damping member 20 is capable of damping axial forces, such as shock, exerted on the coupling member 10 and the sleeve member 30, as shown in FIG. 5.

The second restricting portion 31 has a stepped configuration and includes an upper restricting section 311 and a lower restricting section 312. A shock absorbing ring 36 is mounted against the lower restricting section 312 to cushion impact between the second restricting portion 31 and the upper end surface of the tubular portion 11.

Preferably, a first packing ring 21 is positioned on the first restricting portion 15 to support the lower end of the damping member 20. A second packing ring 35 is positioned between the upper end of the damping member 20 and the upper restricting section 311 of the second restricting portion 31.

The cushioning unit 40 is provided on the coupling member 10 and the sleeve member 30, and includes a resilient cushioning block 42 fitted to the radial outward flange 32 on the lower sleeve portion 301, and an upright retaining member 41 mounted on the mounting plate 12 adjacent to the tubular portion 11. In this embodiment, screws 61 extend through holes 121 in the mounting plate 12 to mount the retaining member 41 on the mounting plate 12. The retaining member 41 confines a vertical slide channel 43 that opens toward the tubular portion 11 and that receives the cushioning block 42, which has an axial length shorter than that of the slide channel 43, slidably therein. The slide channel 43 is formed with an upper limiting surface 411 to limit upward sliding movement of the cushioning block 42 relative to the retaining member 41. Downward sliding movement of the cushioning block 42 in the slide channel 43 is limited by the mounting plate 12. Lubricant may be applied in the slide channel 43 to facilitate sliding movement of the cushioning block 42 therein.

As such, the cushioning unit 40 not only cushions axial and radial (or shear) forces exerted on the coupling member 10 and the sleeve member 30, but also limits relative axial movement between the coupling member 10 and the sleeve member 30. The cushioning unit 40 thus enhances the damping effect of the damping member 20, as shown in FIG. 5.

Figure 3:
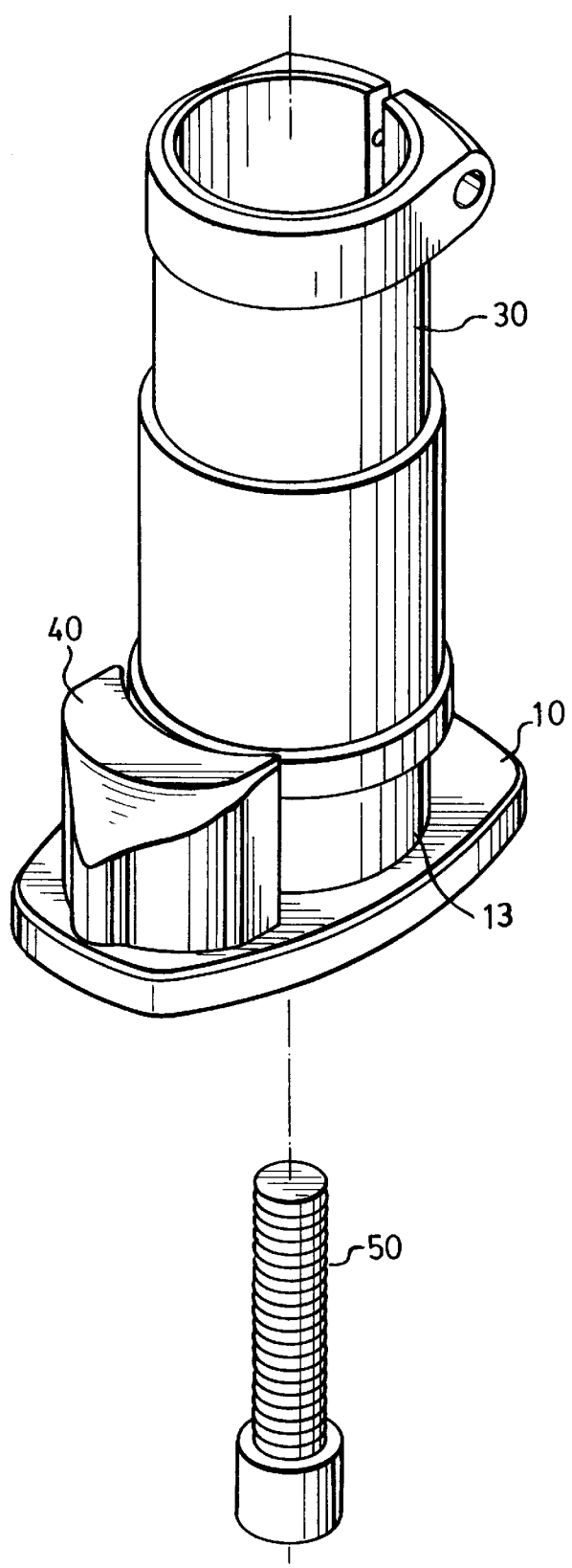
FIG. 3 is a perspective view of the first preferred embodiment.
Figure 4:
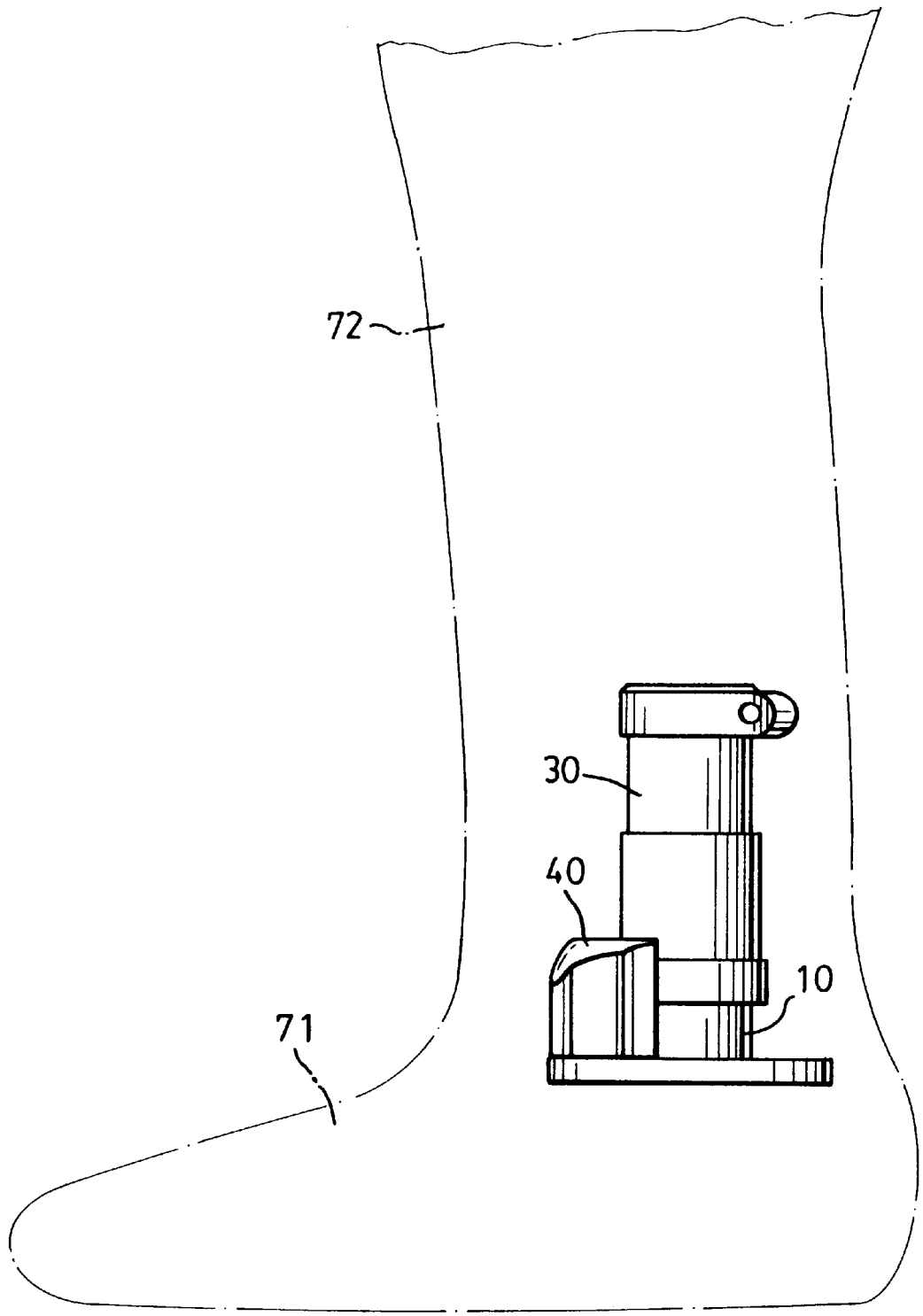
FIG. 4 is a schematic view illustrating how the first preferred embodiment is installed in an artificial lower limb.

Referring to FIGS. 1, 3 and 4, a threaded fastener 50 engages threadedly a mounting hole 14 in the mounting plate 12 to permit fastening of the mounting plate 12 on an artificial foot 71. The upper sleeve portion 302 of the sleeve member 30 can be mounted on a shin 72.

Figure 6:
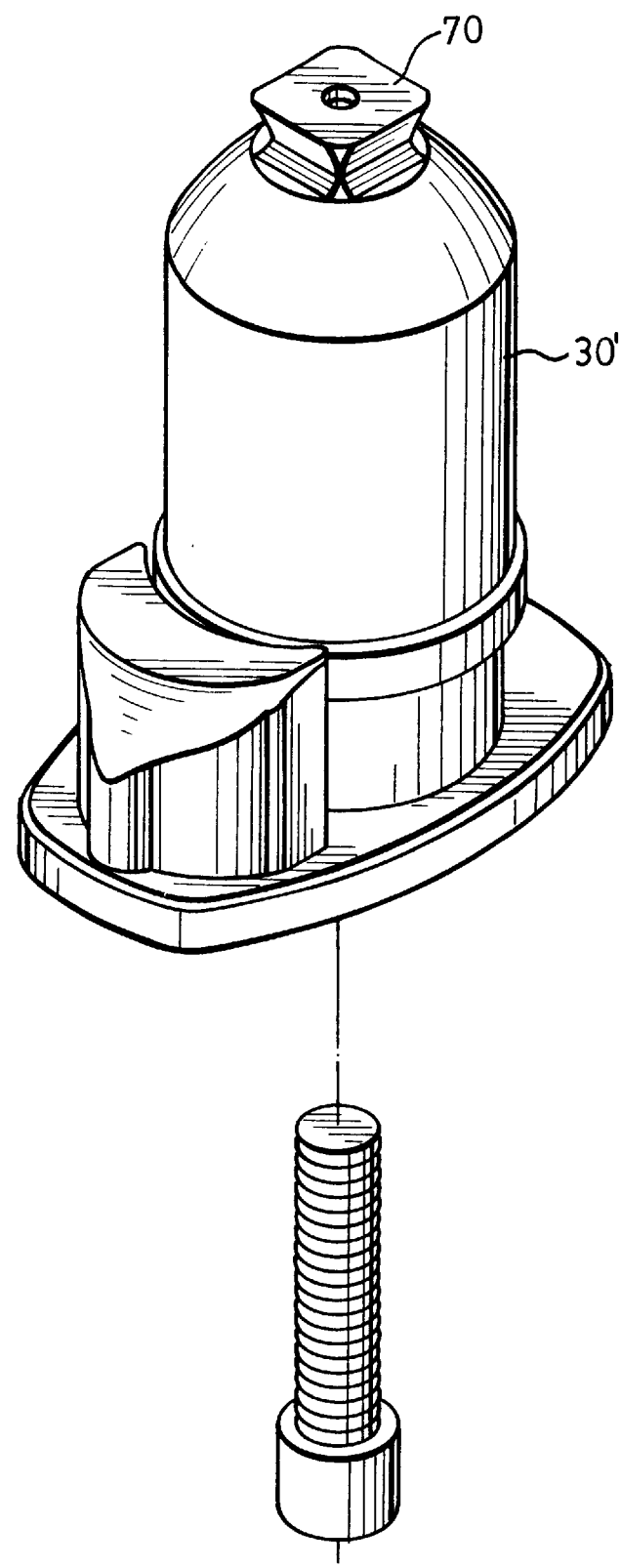
FIG. 6 is a perspective view illustrating a second preferred embodiment of the shock absorbing device according to the present invention.

Referring to FIG. 6, the second preferred embodiment of a shock absorbing device according to this invention is shown to be substantially similar to the previous embodiment, the main difference residing in the structure of the sleeve member 30', which has a spigot 70 adapted for connection to the shin of an artificial lower limb.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A shock absorbing device adapted for use with an artificial leg, comprising:

a coupling member including a horizontal mounting plate and a tubular portion that extends vertically from said mounting plate, said tubular portion having an upper end surface and being formed with a radial inward first restricting portion distal to said upper end surface;

a sleeve member having a lower sleeve portion mounted telescopically on said tubular portion, and an upper sleeve portion formed with a radial inward second restricting portion that is disposed above said upper end surface of said tubular portion of said coupling member;

a damping member extending into said coupling member and said sleeve member, and having a lower end that abuts against said first restricting portion and an upper end that abuts against said second restricting portion, said damping member being capable of damping axial forces exerted on said coupling member and said sleeve member; and a cushioning unit provided on said mounting plate of said coupling member and said lower sleeve portion of said sleeve member for cushioning axial and radial forces exerted on said coupling member and said sleeve member, and for limiting relative axial movement between said coupling member and said sleeve member;

wherein said cushioning unit includes a cushioning block, and an upright retaining member connected to said mounting plate adjacent to said tubular portion, said retaining member confining a vertical slide channel that opens toward said tubular portion and that receives said cushioning block slidably therein, said slide channel being formed with an upper limiting surface to limit upward vertical sliding movement of said cushioning block relative to said retaining member, said upper limiting surface cooperating with said mounting plate to limit the relative axial movement between said coupling member and said sleeve member.

2. The shock absorbing device as claimed in claim 1, wherein said lower sleeve portion is formed with a radial outward flange for mounting said cushioning block thereon.

3. The shock absorbing device as claimed in claim 1, further comprising a lubricating bushing disposed around said tubular portion and inside said lower sleeve portion.

4. The shock absorbing device as claimed in claim 3, further comprising a resilient ring mounted on an inner wall surface of said lower sleeve portion and disposed around and in contact with said lubricating bushing.

5. The shock absorbing device as claimed in claim 1, further comprising a shock absorbing ring mounted on a lower side of said second restricting portion to cushion impact between said second restricting portion and said upper end surface of said tubular portion.

6. The shock absorbing device as claimed in claim 1, wherein said damping member is a compression spring.

7. The shock absorbing device as claimed in claim 1, further comprising fastening means adapted for fastening said mounting plate on an artificial foot, said upper sleeve portion being adapted to be mounted on a shin.

* * * * *